US006781014B1

(12) United States Patent
Vidalin et al.

(10) Patent No.: US 6,781,014 B1
(45) Date of Patent: Aug. 24, 2004

(54) METHANOL PLANT RETROFIT FOR MANUFACTURE OF ACETIC ACID

(75) Inventors: Kenneth Ebenes Vidalin, Vancouver (CA); Daniel Marcel Thiebaut, Cedex (FR)

(73) Assignee: Acetex (Cyprus) Limited, Limassol (CY)

( * ) Notice: Subject to any disclaimer, the term of this patent is extended or adjusted under 35 U.S.C. 154(b) by 85 days.

(21) Appl. No.: 10/129,038

(22) PCT Filed: Oct. 31, 2000

(86) PCT No.: PCT/CY00/00004

§ 371 (c)(1),
(2), (4) Date: Apr. 30, 2002

(87) PCT Pub. No.: WO01/32594

PCT Pub. Date: May 10, 2001

Related U.S. Application Data

(63) Continuation-in-part of application No. 09/430,888, filed on Nov. 1, 1999, now Pat. No. 6,274,096, and a continuation-in-part of application No. 09/547,831, filed on Apr. 12, 2000, now Pat. No. 6,232,352, which is a continuation-in-part of application No. 09/430,808, filed on Nov. 1, 1999, now Pat. No. 6,274,096.

(51) Int. Cl.[7] ............................................. C07C 53/08
(52) U.S. Cl. ........................ 562/607; 560/232; 560/241; 252/373
(58) Field of Search ............................. 562/512, 512.2, 562/517, 519, 522, 606, 607, 609; 560/129, 231, 232, 239, 241; 518/702, 712, 728

(56) References Cited

U.S. PATENT DOCUMENTS

| | | |
|---|---|---|
| 1,961,736 A | 6/1934 | Carlin et al. ................ 260/116 |
| 2,622,089 A | 12/1952 | Mayland ...................... 252/373 |
| 2,727,064 A | 12/1955 | Thomas et al. ............. 260/532 |
| 3,442,613 A | 5/1969 | Grotz ........................... 23/199 |
| 3,769,329 A | 10/1973 | Paulik et al. ............... 260/488 |
| 3,859,230 A | 1/1975 | Moe ............................ 252/373 |
| 4,081,253 A | 3/1978 | Marion ......................... 48/197 |
| 4,110,359 A | 8/1978 | Marion ....................... 260/449 |
| 4,175,115 A | 11/1979 | Ball et al. ................... 423/415 |
| 4,316,880 A | 2/1982 | Heinz et al. ................ 423/415 |
| 4,780,300 A | 10/1988 | Yokoyama et al. ......... 423/415 |
| 4,833,171 A | 5/1989 | Sweeney ..................... 518/703 |
| 4,891,950 A | 1/1990 | Seufert et al. ................ 62/37 |
| 4,994,603 A | 2/1991 | Mueller et al. ............. 560/232 |
| 5,104,419 A | 4/1992 | Funk ........................... 48/209 |
| 5,189,203 A | 2/1993 | Hansen et al. ............. 560/232 |
| 5,281,751 A | 1/1994 | Schreck ...................... 562/519 |
| 5,488,143 A | 1/1996 | Uhm et al. ................. 560/232 |
| 5,653,774 A | 8/1997 | Bhattacharyya et al. ...... 48/198 |
| 5,728,871 A | 3/1998 | Joensen et al. ............ 562/519 |
| 5,767,165 A | 6/1998 | Steinberg et al. .......... 518/703 |
| 5,773,642 A | 6/1998 | Denis et al. ................ 560/232 |
| 5,817,869 A | 10/1998 | Hinnenkamp et al. ...... 562/519 |
| 5,840,969 A | 11/1998 | Joensen ...................... 562/519 |
| 5,855,815 A | 1/1999 | Park et al. .................. 252/373 |
| 5,877,347 A | 3/1999 | Ditzel et al. ................ 562/519 |
| 5,877,348 A | 3/1999 | Ditzel et al. ................ 562/519 |
| 5,883,289 A | 3/1999 | Denis et al. ................ 560/232 |
| 5,883,295 A | 3/1999 | Sunley et al. .............. 562/519 |
| 6,048,508 A | 4/2000 | Dummersdorf et al. ..... 423/210 |
| 6,171,574 B1 | 1/2001 | Juda et al. ............... 423/648.1 |
| 6,232,352 B1 | 5/2001 | Vidalin ....................... 518/700 |
| 6,274,096 B1 | 8/2001 | Thiebaut et al. ........... 422/148 |
| 6,353,133 B1 | 3/2002 | Thiebaut et al. ........... 562/519 |
| 2002/0085963 A1 | 7/2002 | Vidalin ....................... 422/187 |

FOREIGN PATENT DOCUMENTS

| | | |
|---|---|---|
| DE | 3712008 | 10/1988 |
| EP | 0845452 | 6/1998 |

OTHER PUBLICATIONS

"Sulfur Passivated Reforming Process Lowers Syngas H2/CO Ratio"; Udengaard, Niels R., Hansen, Jens Henrik Bak; Hanson, David C. and Stat, Joseph A. ; *Oil & Gas Journal*, pp. 62–67 (Mar. 9, 1992).

"The First Commercial Sulfur Passivated Reforming (SPARG) Plant"; Hanson, D.C. and Stal, J.A.; 1990 Topsoe Seminar on Synthesis Gas Technologies, pp 1–13 (1990).

"Low Stream/Gas Ratios in Reforming"; Evans, P.W. and Hanson, D.C.; American Institute of Chemical Engineers Ammonia Symposium; AICHE Paper No. 51f, (Aug. 1985).

*Primary Examiner*—Shailendra Kumar
*Assistant Examiner*—Karl Puttlitz
(74) *Attorney, Agent, or Firm*—Daniel N. Lundeen; Lundeen & Dickinson LLP

(57) ABSTRACT

The retrofitting of an existing methanol or methanol/ammonia plant to make acetic acid is disclosed. The existing plant has a reformer (10) to which natural gas or another hydrocarbon and steam (water) are fed. Syngas is formed in the reformer (10). All or part of the syngas is process to separate out carbon dioxide (24), carbon monoxide (30) and hydrogen (32), and the separated carbon dioxide (24) is the existing to the existing methanol synthesis loop (12) for methanol synthesis, or back into the feed to the reformer (10) to enhance carbon monoxide formation in the syngas (18). Any remaining syngas (38) not fed to the carbon dioxide separator (22) can be converted to methanol in the existing methanol synthesis loop (12) along with carbon dioxide (24) from the separator (22) and/or imported carbon dioxide (25), and hydrogen (35) from the separator (28). The separated carbon monoxide (30) is then reacted with the methanol (36) to produce acetic acid (40) or an acetic acid precursor by a conventional process. Also disclosed is the reaction of separated hydrogen (32) with nitrogen (52), in a conventional manner, to produce ammonia. Also disclosed is the reaction of a portion of the acetic acid (40) in a conventional manner with oxygen (46) and ethylene (44) to form vinyl acetate monomer (48). The nitrogen for the added ammonia capacity in a retrofit of an original methanol plant comprising an ammonia synthesis loop (33), and the oxygen (46) for the vinyl acetate monomer process (42), are obtained from a mew air separation unit (50).

16 Claims, 6 Drawing Sheets

US 6,781,014 B1

METHANOL PLANT RETROFIT FOR MANUFACTURE OF ACETIC ACID

CROSS REFERENCE TO RELATED APPLICATION

This application is a 371 of PCT/CY00/00004, filed Oct. 31, 2000, which is a continuation-in-part of Ser. No. 09/430,888 now U.S. Pat. No. 6,274,096 filed Nov. 1, 1999, and is a continuation-in-par of Ser. No. 09/547,831 filed Apr. 12, 2000 now U.S. Pat. No. 6,232,352, which is a continuation-in-part of Ser. No. 09/430,888 filed Nov. 1, 1999 U.S. Pat. No. 6,274,096.

FIELD OF THE INVENTION

The present invention is directed generally to a process for making synthesis gas from which streams of carbon monoxide and methanol can be obtained for the manufacture of acetic acid, and more particularly to the retrofit of a methanol plant to divert all or a portion of the syngas from the existing methanol synthesis loop to a carbon monoxide separator and to react the methanol from the methanol synthesis loop with the carbon monoxide from the separator in approximately stoichiometric proportions to directly or indirectly make acetic acid.

BACKGROUND OF THE INVENTION

The manufacture of acetic acid from carbon monoxide and methanol using a carbonylation catalyst is well known in the art. Representative references disclosing this and similar processes include U.S. Pat. No. 1,961,736 to Carlin et al (Tennessee Products); U.S. Pat. No. 3,769,329 to Paulik et al (Monsanto); U.S. Pat. No. 4,081,253 to Marion (Texaco Development Corporation); U.S. Pat. No. 5,155,261 to Marston et al (Reilly Industries); U.S. Pat. No. 5,672,743 to Garland et al (PB Chemicals); U.S. Pat. No. 5,728,871 to Joensen et al (Haldor Topsoe); U.S. Pat. No. 5,773,642 289 to Denis et al (Acetex Chimie); U.S. Pat. No. 5,817,869 to Hinnenkamp et al (Quantum Chemical Corporation); U.S. Pat. Nos. 5,877,347 and 5,877,348 to Ditzel et al (BP Chemicals); U.S. Pat. No. 5,883,289 to Denis et al (Acetex Chimie); and U.S. Pat. No. 5,883,295 to Sunley et al (BP Chemicals); and EP 845,452-A (Topsoe Haldor. AS) and DE 3712008-A (Linde AG).

The primary raw materials for acetic acid manufacture are, of course, carbon monoxide and methanol. In the typical acetic acid plant, methanol is imported and carbon monoxide, because of difficulties associated with the transport and storage thereof, is generated in situ, usually by reforming natural gas or another hydrocarbon with steam and/or carbon dioxide. A significant expense for new acetic acid production capacity is the capital cost of the equipment necessary for the carbon monoxide generation. It would be extremely desirable if this capital cost could be largely eliminated or significantly reduced.

Market conditions, from time to time in various localities, can result in relatively low methanol prices (an oversupply) and/or high natural gas prices (a shortage) that can make methanol manufacture unprofitable. Operators of existing methanol manufacturing facilities can be faced with the decision of whether or not to continue the unprofitable manufacture of methanol in the hope that product prices will eventually rebound and/or raw material prices will drop to profitable levels. The present invention addresses a way of modifying an existing unprofitable methanol plant to make it more profitable when methanol prices are low and/or gas prices are high.

As far as applicant is aware, there is no disclosure in the prior art for modifying existing methanol plants, including methanol/ammonia plants, to supply stoichiometric MeOH and CO for manufacturing acetic acid, for example, that can be a more valuable product than MeOH.

SUMMARY OF THE INVENTION

The present invention involves the discovery that the large capital costs associated with CO generation for a new acetic acid plant can be significantly reduced or largely eliminated by retrofitting an existing methanol or methanol/ammonia plant to make acetic acid. All or part of the syngas is diverted from the MeOH synthesis loop and supplied instead to a separator unit to recover $CO_2$, CO and hydrogen, which are advantageously used in various novel ways to produce acetic acid. The recovered $CO_2$ can be supplied to the reformer to enhance CO production, or to the MeOH synthesis loop to make methanol. The recovered CO is usually supplied to the acetic acid reactor with the methanol to make the acetic acid. The recovered hydrogen can be supplied to the MeOH loop for methanol production, used for the manufacture of ammonia or other products, burned as a fuel, or exported, since the hydrogen is normally produced in excess of the requirements for methanol synthesis in the present invention.

The carbon dioxide can be fed into a catalytic reformer to which natural gas and steam (water) are fed. Syngas is formed in the reformer wherein both the natural gas and the carbon dioxide are reformed to produce syngas with a large proportion of carbon monoxide relative to reforming without added carbon dioxide. Alternatively or additionally, the $CO_2$ can be supplied to the MeOH loop, with additional CO from the synthesis gas and/or additional import d $CO_2$, for catalytic reaction with hydrogen to make methanol.

The syngas can be split into a first part and a second part. The first syngas part is converted to methanol in a conventional methanol synthesis loop that is operated at half of the design capacity of the original plant since less syngas is supplied to it. The second syngas part can be processed to separate out carbon dioxide and carbon monoxide, and the separated carbon dioxide can be fed back into the feed to the reformer to enhance carbon monoxide formation, and/or fed to the MeOH synthesis loop to make methanol. The separated carbon monoxide can then be reacted with the methanol to produce acetic acid or an acetic acid precursor by a conventional process.

Separated hydrogen, which is generally produced in excess beyond that required for methanol synthesis in the present process, can also be reacted with nitrogen, in a conventional manner, to produce ammonia. Also, a portion of acetic acid that is produced can be reacted in a conventional manner with oxygen and ethylene to form vinyl acetate monomer. The nitrogen for the ammonia process (especially for any added ammonia capacity in a retrofit of an original methanol plant comprising an ammonia synthesis loop) and the oxygen for the vinyl acetate monomer process, can be obtained from a conventional air separation unit.

Broadly, the present invention provides, in one aspect, a method for retrofitting an original methanol plant which has at least one steam reformer for converting a hydrocarbon to a syngas stream containing hydrogen and carbon monoxide, a heat recovery section for cooling the syngas stream, a compression unit for compressing the syngas stream, and a methanol synthesis loop for converting at least a portion of the hydrogen and carbon monoxide in the syngas stream to methanol. The method converts the methanol plant into a retrofitted plant for manufacturing a product from carbon monoxide and methanol selected from the group consisting of acetic acid, acetic anhydride, methyl formate, methyl acetate and combinations thereof. The method comprises the steps of: (a) diverting a portion of the syngas stream from at least one reformer to a separation unit; (b) operating the methanol synthesis loop with a feed comprising the remaining syngas stream to produce less methanol than the original methanol plant; (c) operating the separation unit to separate the diverted syngas into at least a carbon monoxide-rich stream and a hydrogen-rich stream, wherein the quantity of hydrogen in the hydrogen-rich stream is greater than any net hydrogen production of the original methanol plant; and (d) reacting the carbon monoxide-rich stream from the separation unit with the methanol from the methanol synthesis loop to form the product, wherein the diversion of the syngas stream is balanced for production of the methanol from the methanol synthesis loop and the carbon monoxide-rich stream from the separation unit for stoichiometric conversion to the product.

Preferably, at least one steam reformer is modified to increase carbon monoxide production in the syngas stream. The syngas stream preferably comprises canon dioxide, and the separation unit produces a carbon dioxide-rich stream that is preferably recycled to at least one reformer to increase the carbon monoxide production.

The reaction step can include the direct catalytic reaction of methanol and carbon monoxide to form acetic acid as in the Mosanto-BP process, for example, or alternatively can comprise the intermediate formation of methyl formate and isomerization of the methyl formate to acetic acid, the intermediate reaction of CO and two moles of methyl alcohol to form methyl acetate and hydrolysis of the methyl acetate, to acetic acid and methanol, or the carbonylation of the methyl acetate to form acetic anhydride.

In one preferred embodiment of the retrofitting method, the present invention provides a method for retrofitting an original methanol plant that has at least one steam reformer for converting a hydrocarbon/steam feed to a syngas stream containing hydrogen and carbon monoxide, a heat recovery section for cooling the, syngas stream, a compression unit for compressing the syngas stream, and a methanol synthesis loop for converting at least a portion of the hydrogen and carbon monoxide in the syngas stream to methanol. The retrofitted plant can manufacture a product from carbon monoxide and methanol selected from the group consisting of acetic acid, acetic anhydride, methyl formate, methyl acetate and combinations thereof. The retrofitting method comprises the steps of: (a) modifying at least one steam reformer for operation with a feed comprising a relatively increased carbon dioxide content; (b) div rting a portion of the syngas stream from at least one steam reformer to a separation unit; (c) operating the methanol synthesis loop with a feed comprising the remaining syngas stream to produce less methanol than the original methanol plant; (d) operating the separation unit to separate the diverted syngas into a carbon dioxide-rich stream, a carbon monoxide-rich stream and a hydrogen-rich stream; (e) recycling the carbon dioxide-rich stream from the separation unit to at least one modified steam reformer to increase the carbon monoxide formation relative to the original methanol plant and increase the molar ratio of carbon monoxide to hydrogen; (f) reacting the carbon monoxide-rich stream from the separation unit with the methanol from the methanol synthesis loop to form the product, wherein the diversion of the syngas stream is balanced for the production of the methanol from the methanol synthesis loop and the carbon monoxide-rich stream from the separation unit for stoichiometric conversion to the product.

The modified steam reformer is preferably modified to operate at a higher temperature to enhance the carbon conversion to carbon monoxide. The separation unit can include a solvent absorber and stripper for carbon dioxide recovery, and a cryogenic distillation unit for carbon monoxide and hydrogen recovery.

The compression unit preferably has a three-stage compressor, and the syngas stream diversion preferably occurs between the second and third compression stages. The third compressor stage is preferably modified for operation at a lower throughput than the original methanol plant. Where the methanol synthesis loop of the original methanol plant includes a recycle loop compressor, the recycle loop compressor can also be modified for operation at a lower throughput.

The method can also comprise importing a stream of mixed CO/carbon dioxide stream, for example in a 1:2 to 2:1 molar ratio. The imported stream can be supplied to the methanol synthesis loop or to the separation unit, but is preferably supplied to the reformer wherein the carbon dioxide therein is converted to CO.

The method can further comprise the step of reacting the hydrogen in the hydrogen-rich stream with nitrogen to make ammonia. Where the original methanol plant produces a hydrogen-rich stream comprising a loop purge from the methanol synthesis loop that was reacted with nitrogen to make ammonia, the retrofitted plant can use the hydrogen-rich stream from the separation unit as a primary hydrogen source for the ammonia production. With the additional hydrogen available from the syngas, additional ammonia can be produced in the retrofitted plant relative to the original methanol plant.

The method can further comprise installing a vinyl acetate monomer unit for reacting a portion of the acetic acid with ethylene and oxygen to make vinyl acetate monomer. An air separation unit can be installed to make the oxygen for the vinyl acetate monomer unit, and the nitrogen produced from the air separation unit preferably matches the nitrogen required for the additional ammonia production.

In another aspect, the present invention provides a process for making hydrogen and a product selected from the group consisting of acetic acid, acetic anhydride, methyl formate, methyl acetate and combinations thereof, from a hydrocarbon via methanol and carbon monoxide which can be effected by construction of a new plant or retrofit of an existing plant. The process comprises the steps of, (a) catalytically reforming the hydrocarbon with steam in the presence of a minor proportion of carbon dioxide to form a syngas containing hydrogen, carbon monoxide, and carbon dioxide having a molar ratio of R $((H_2-CO_2)/(CO+CO_2))$ from 2.0 to 2.9; (b) recovering heat from the syngas to form a cooled syngas stream; (c) compressing the cooled syngas stream to a separation pressure; (d) diverting a major portion of the compressed syngas to a separation unit (e) separating the syngas diverted to the separation unit into a carbon-dioxide-rich stream, a carbon monoxide-rich stream and a hydrogen-rich stream; (f) recycling the: carbon dioxide-rich stream to the reforming step; (g) further compressing the remaining minor portion of the syngas to a methanol synthesis pressure higher than the separation pressure; (h) operating a methanol synthesis loop to convert the hydrogen and carbon monoxide in the further compressed syngas into a methanol stream; and (i) reacting the carbon monoxide-rich stream from the separation unit with the methanol stream from the methanol synthesis loop to make the product. The diversion step is preferably balanced to obtain stoichiometric amounts of carbon monoxide and methanol.

The process preferably has a molar ratio of carbon dioxide to hydrocarbon comprising natural gas in feed to the reforming step from 0.1 to 0.5 and a ratio of steam to natural gas from 2 to 6. The methanol synthesis loop can be operated below a total maximum capacity of the methanol synthesis loop. The process can further comprise the step of reacting the hydrogen in the hydrogen-rich stream with nitrogen in an ammonia synthesis reactor to make ammonia. The process can also comprise the step of separating air into a nitrogen stream and an oxygen stream and supplying the nitrogen stream to the ammonia synthesis reactor. Where the product comprises acetic acid or an acetic acid precursor which is converted to acetic acid, the process can further comprise the step of supplying the oxygen stream from the air separation unit to a vinyl acetate synthesis reactor, along with a portion of the acetic acid from the carbon monoxide-methanol reaction step, and ethylene, to produce a vinyl acetate monomer stream.

In a further aspect the present invention provides a method for retrofitting an original methanol plant, comprising at least one steam reformer for converting a hydrocarbon to a syngas stream containing hydrogen, carbon monoxide, and carbon dioxide, and a methanol synthesis loop for converting hydrogen and carbon monoxide from the syngas stream to methanol, into a retrofitted plant for manufacturing a product from carbon monoxide and methanol selected from the group consisting of acetic acid, acetic anhydride, methyl formate, methyl acetate and combinations thereof. The method includes (1) separating all or part of the syngas stream in a separation unit into respective streams rich in carbon dioxide, carbon monoxide and hydrogen; (2) operating the methanol synthesis loop with a feed comprising (a) carbon dioxide and (b) a portion of the hydrogen-rich stream; and (3) reacting at least a portion of the carbon monoxide-rich stream from the separation unit with methanol from the methanol synthesis loop to form the product. The feed to the methanol synthesis loop can include imported carbon dioxide and/or a portion of the synthesis gas. Preferably, all of the syngas stream is supplied to the separation step. The amount of the hydrogen-rich stream is generally in excess of the stoichiometric hydrogen required by the methanol synthesis loop. Preferably, all of the carbon dioxide-rich stream is supplied to the synthesis loop, and all of the carbon monoxide-rich stream to the reaction step.

In a preferred embodiment, the retrofitting method comprises (1) supplying a major portion of the syngas stream to a separation unit for separating the syngas stream into respective streams rich in carbon dioxide, carbon monoxide and hydrogen, (2) operating the methanol synthesis loop with a feed comprising the carbon-dioxide-rich stream from the separation unit, a minor portion of the syngas stream, and an additional source of carbon dioxide to produce a methanol stream, and (3) reacting the carbon monoxide-rich stream from the separation unit with the methanol stream from the methanol synthesis loop to form the product.

In another preferred embodiment, the retrofitting method comprises (1) supplying the syngas stream to a separation unit for separating the syngas stream into respective streams rich in carbon dioxide, carbon monoxide and hydrogen, (2) operating the methanol synthesis loop with a feed comprising the carbon-dioxide-rich stream from the separation unit, a portion of the hydrogen-rich stream from the separation unit, a minor portion of the syngas stream, and carbon dioxide from an additional source, to produce a methanol stream, and (3) reacting the carbon monoxide-rich stream from the separation unit with the methanol stream from the methanol synthesis loop in stoichiometric proportions to form the product.

In a further preferred embodiment, the retrofitting method comprises importing a stream of mixed CO/carbon dioxide stream, for example in a 1:2 to 2:1 molar ratio. The imported stream can be supplied to the methanol synthesis loop or to the separation unit, but is preferably supplied to the reformer for conversion of the carbon dioxide to CO.

In yet another aspect, the present invention provides a process for making hydrogen and a product selected from the group consisting of acetic acid, acetic anhydride, methyl formate, methyl acetate and combinations thereof, from a hydrocarbon via intermediate methanol, carbon monoxide, and carbon dioxide. The process includes (1) reforming the hydrocarbon with steam to form a syngas containing hydrogen, carbon monoxide, and carbon dioxide, (2) recovering heat from the syngas to form a cooled syngas stream, (3) compressing the cooed syngas stream to a separation pressure, (4) processing the syngas in a separation unit to separate a carbon monoxide-rich stream from the hydrogen and carbon dioxide, (5) operating a methanol synthesis loop to react a first portion of the hydrogen from the separation unit with the carbon dioxide from the separation unit, and additional carbon dioxide from another source, to obtain a methanol stream, (6) reacting the carbon monoxide-rich stream from the separation unit with the methanol stream from the methanol synthesis loop in stoichiometric proportions to form a product selected from the group consisting of acetic acid, acetic anhydride, methyl formate, methyl acetate and combinations thereof.

Regardless of whether the plant is a retrofit or a new plant, where the product comprises acetic acid, the reaction step preferably comprises reacting methanol, methyl formate, or a combination thereof in the presence of a reaction mixture comprising carbon monoxide, water, a solvent and a catalyst system comprising at least one halogenated promoter and at least one compound of rhodium, iridium or a combination thereof. The reaction mixture preferably has a water content up to 20 weight percent Where the reaction step comprises simple carbonylation, the water content in the reaction mixture is more preferably from 14 to 15 weight percent. Where the reaction step comprises low-water carbonylation, the water content in the reaction mixture is more preferably from 2 to 8 weight percent. Where the reaction step comprises methyl formate isomerization or a combination of isomerization and methanol carbonylation, the reaction mixture more preferably contains a nonzero quantity of water up to 2 weight percent. The reaction step is preferably continuous.

DETAILED DESCRIPTION OF THE INVENTION

Figure 1:
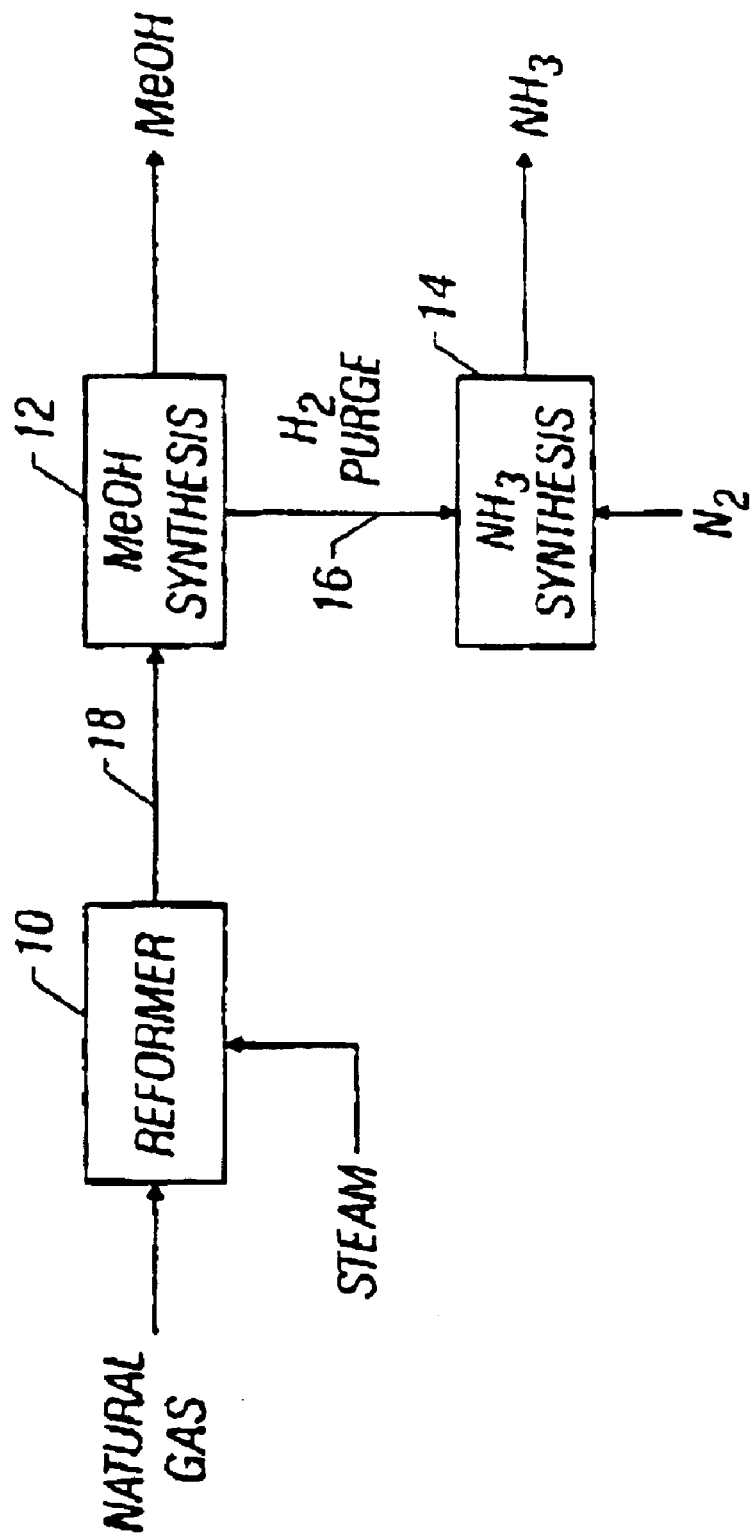
FIG. 1 (prior art) is an overall block flow diagram of a typical methanol/ammonia plant using hydrogen from the methanol synthesis loop purge to make ammonia, which can be retrofitted according to the present invention for acetic acid manufacture.

With reference to FIG. 1, an original plant which can be retrofitted according to one embodiment of the present invention has an existing conventional steam reformer unit 10, methanol (MeOH) synthesis unit 12 and preferably ammonia synthesis unit 14 wherein hydrogen for the ammonia synthesis unit 14 is taken as purge stream 16 from the methanol synthesis loop. The retrofit of the present invention is generally applicable to any plant that generates and uses synthesis gas to make methanol. As used in the present specification and claims, reference to "original plant" shall mean the plant as built and including any intervening modifications prior to the retrofit of the present invention.

The reformer unit 10 is typically a fired furnace containing parallel tube banks filled with conventional reforming catalyst such as alumina-supported nickel oxide, for example. The feed to the reformer(s) is any conventional reformer feed such as a lower hydrocarbon, typically naphtha or natural gas. The reformer can be a single-pass reformer or a two-stage reformer, or any other commercially available reformer, such as, for example, a KRES unit available from Kellogg, Brown & Root, as is known to those skilled in the art. The reformer effluent of the original methanol plant can contain any conventional H$_2$:CO ratio, but is normally close to 2.0 in plants making solely methanol, and higher, e.g. 3.0 and above, in plants producing a separate hydrogen product or intermediate hydrogen-containing stream, e.g. for ammonia synthesis. The hydrogen-containing stream is typically obtained as purge stream 16 from the methanol synthesis unit 12 loop which is necessary to keep the level of hydrogen and inerts from building up in the synthesis gas recirculated through the methanol synthesis unit 12.

Figure 2:
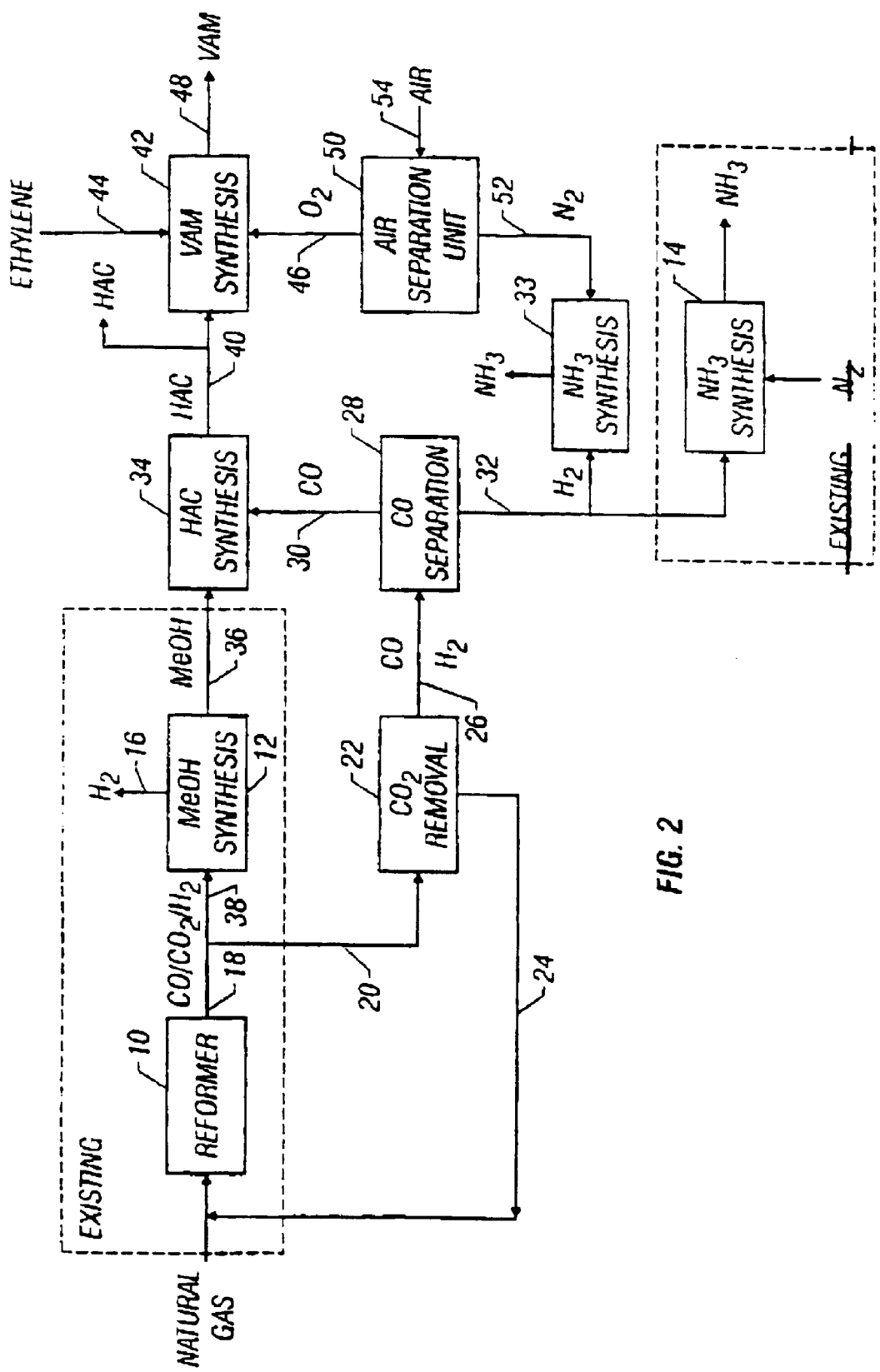
FIG. 2 is an overall block flow diagram of the plant of FIG. 1 after it has been retrofitted according to the present invention to make acetic acid, vinyl acetate monomer and additional ammonia.

According to the present invention, the original plant of FIG. 1 is retrofitted to produce acetic acid (HAC) using the existing reformer 10 and methanol synthesis unit 12, and keeping any ammonia synthesis unit 14, as shown in FIG. 2. A portion of the effluent 18 from the reformer 10 is diverted from the methanol so synthesis unit 12 via line 20 to a new CO$_2$ removal unit 22. The CO$_2$ removal unit 22 separates the stream from line 20 into a CO$_2$-rich stream 24 and a CO$_2$-lean stream 26 using conventional CO$_2$ separation equipment and methodology such as, for example, absorption-stripping with a solvent such as water, methanol, generally aqueous alkanolamines such as ethanolamine, diethanolamine, methyidiethanolamine and the like, aqueous alkali carbonates such as sodium and potassium carbonates, and the like. Such CO$_2$ absorption-stripping processes are commercially available under the trade designations Girbotol, Sulfinol, Rectisol, Purisol, Fluor, BASF (aMDEA) and the like.

The CO$_2$ recovered from the CO$_2$ removal unit 22 or from another source can be supplied to the reformer 10. Increasing the CO$_2$ in the feed to the reformer 10 increases the CO content of the effluent 18. Analogous to steam reforming where a hydrocarbon reacts with steam to form synthesis gas, the reaction of the hydrocarbon with carbon dioxide is often called CO$_2$ reforming. As the carbon dioxide content of the reformer feed is increased, the share of the carbon in the carbon monoxide in the product synthesis gas 18 that is supplied from the carbon dioxide increases in relative proportion and the share originating from the hydrocarbon decreases. So, for a given CO production rate, the hydrocarbon feed gas requirement is reduced. During the early stage of reforming, heavier hydrocarbons are converted to methane:

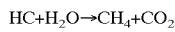

The main steam and CO$_2$ reforming reactions convert methane to hydrogen and carbon monoxide:

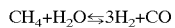

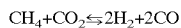

The shift reaction converts carbon monoxide to carbon dioxide and more hydrogen:

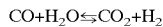

The conversion of the heavier hydrocarbons goes to completion. The steam reforming, CO$_2$ reforming, and shift reaction are equilibrium-restricted. The overall reaction is strongly endothermic. The reformer 10 can, if desired, be modified for additional heat input for supplemental CO$_2$ reforming and additional heat recovery. The effluent 18 from the modified reformer 10 has a molar ratio of hydrogen minus CO$_2$ to CO plus CO$_2$ (referred to in the present specification and claims as the "R ratio" (H$_2$−CO$_2$)/(CO+CO$_2$)), which can be optimized for methanol synthesis, preferably within the range from 2.0 to 2.9. The possibility of optimizing the R ratio arises from the discovery that the hydrogen for the ammonia synthesis no longer needs to be obtained as the methanol purge stream 16, but can instead be recovered from the syngas diverted via line 20 as discussed in more detail below.

The CO$_2$-lean stream 26 contains primarily CO and hydrogen and can be separated in CO separation unit 28 into a CO-rich stream 30 and a hydrogen-rich stream 32. The separation unit 28 can comprise any equipment and/or methodologies for separating the CO/hydrogen mixture into relatively pure CO and hydrogen streams, such as, for example, semi-permeable membranes, cryogenic fractionation, or the like. Cryogenic fractional distillation is preferred, and can include simple partial condensation without any columns, partial condensation with columns, optionally with a pressure swing absorption (PSA) unit and a hydrogen recycle compressor, or methane wash. Normally, partial condensation with columns is sufficient for obtaining CO and hydrogen of sufficient purity for acetic acid and ammonia production, respectively, keeping equipment and operating costs to a minimum, although the PSA unit and hydrogen recycle compressor can be added for increasing the hydrogen purity and CO production rate. For acetic acid manufacture, the CO stream 30 preferably contains less than 1000 ppm hydrogen and less than 2 mole percent nitrogen plus methane. For ammonia production, the hydrogen stream 32 which is sent to a nitrogen wash unit (not shown) preferably contains at least 80 mol % hydrogen, more preferably at least 95 mol % hydrogen.

A portion of the hydrogen stream 32 is supplied to the existing ammonia synthesis unit 14 in place of the methanol loop purge stream 16. The quantity of hydrogen produced in the stream 32 is generally much larger than the amount previously supplied via line 16. This is due in large part to the fact that less methanol is made in the retrofitted plant, and thus less hydrogen is consumed for methanol synthesis. The additional hydrogen capacity can be used as a fuel supply, or as a raw hydrogen source for another process, such as, for example, increased ammonia conversion. Additional ammonia can be made by supplying a portion of the additional, hydrogen to the existing ammonia synthesis reactor 14 where the ammonia conversion capacity can be increased, and/or by installing additional ammonia synthesis unit 33. The increased ammonia capacity can be complemented by the presence of existing ammonia handling, storage and transport facilities which may be able to accommodate the additional ammonia capacity with little or no modification.

The methanol synthesis unit 12 is a conventional methanol conversion unit such as, for example, an ICI reactor. The methanol synthesis unit 12 of the retrofitted plant shown in FIG. 2 is essentially the same as in the original plant prior to the retrofit, except that the quantity of methanol produced is lower, preferably half of that of the original plant. Concomitantly, the loop recycle compressor (not shown) is operated at a lower capacity and the purge stream 16 is considerably reduced in quantity. As mentioned above, the purge stream 16 is no longer needed for supplying the hydrogen to the ammonia converter 14, since this is now supplied in the retrofitted plant from the hydrogen stream 32 separated directly from the portion of the reformer 10 effluent 18 diverted from the feed to the methanol synthesis unit 12 via line 20. If desired, the purge stream 16 can now be used for fuel and/or as a hydrogen source for hydrodesulfurization of the feed to the reformer 10. Since there is no longer any need to pass the excess hydrogen through the methanol synthesis unit 12 for use in the ammonia unit 14, the feed to the methanol synthesis unit 12, i.e. the effluent 18, can be compositionally optimized for more efficient methanol conversion, as described above. It can also be desirable to modify the methanol synthesis unit 12, if desired during the retrofit, to include any other modifications which are not present in the original plant but have become conventional and have been developed for methanol synthesis loops since the construction of the original plant and have not previously been incorporated therein.

The amount of syngas in the effluent 18 from the reformer 10 which is diverted to $CO_2/CO/H_2$ separation is preferably balanced to provide a stoichiometric ratio of methanol and CO to produce acetic acid therefrom in acetic acid synthesis unit 34. Preferably, the ratio of CO in line 30 and methanol in line 36 is equal or the methanol is produced at a 10–20% molar excess, e.g. a molar ratio from 1.0 to 1.2. To produce this ratio of methanol and CO, a relatively larger quantity (total kg/hr) of the effluent 18 is diverted into line 20, and the remaining minor portion is fed in line 38 to the methanol synthesis unit 12.

The acetic acid synthesis unit 34 employs conventional acetic acid manufacturing equipment and methodology well known and/or commercially available to those skilled in the art, such as, for example, from one or more of the acetic acid manufacturing patents mentioned above. For example, a conventional BP/Monsanto process can be employed, or an improved BP/Monsanto process employing BP-Cativa technology (iridium catalyst), Celanese low water technology (rhodium-lithium acetate catalyst), Millenium low water technology (rhodium-phosphor oxides catalyst), Acetex technology (rhodium-iridium catalyst) and/or dual process methanol carbonylation-methyl formate isomerization. The reaction generally comprises reacting methanol, methyl formate, or a combination thereof in the presence of a reaction mixture comprising carbon monoxide, water, a solvent and a catalyst system comprising at least one halogenated promoter and at least one compound of rhodium, iridium or a combination thereof. The reaction mixture preferably has a water content up to 20 weight percent. Where the reaction comprises simple carbonylation, the water content in the reaction mixture is preferably from 14 to 15 weight percent. Where the reaction comprises low-water carbonylation, the water content in the reaction mixture is preferably from 2 to 8 weight percent. Where the reaction comprises methyl formate isomerization or a combination of isomerization and methanol carbonylation, the reaction mixture preferably contains a nonz ro quantity of water up to 2 weight percent. The reaction is typically continuous. An acetic acid product is obtained via line 40.

If desired, a portion of the acetic acid from line 40 can be fed to a conventional vinyl acetate monomer synthesis unit 42 where it is reacted with ethylene via line 44 and oxygen via line 46 to obtain monomer product stream 48. The oxygen in line 46 can be obtained, for example, using a conventional (preferably cryogenic) air separation unit 50 which also produces a nitrogen stream 52 corresponding to the amount of air from line 54 needed for the oxygen in line 46. The amount of air separated can be matched to produce the nitrogen required via line 52 for the additional ammonia capacity added by ammonia synthesis unit 33 as mentioned above.

Figure 5:
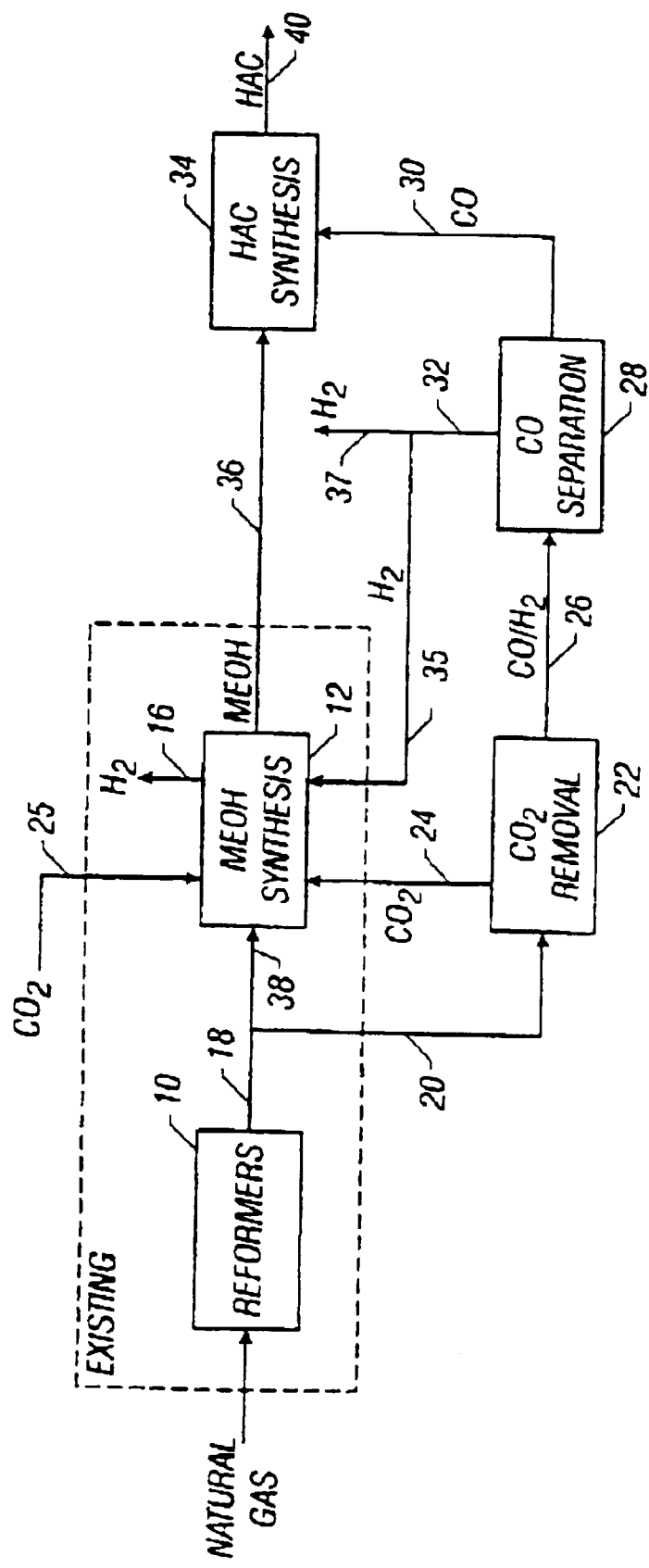
FIG. 5 is an overall block flow diagram of the plant of FIG. 1 after it has been retrofitted according to an alternate embodiment of the present Invention wherein a portion of the syngas stream is diverted to separation and the MeOH synthesis loop is supplied with hydrogen and CO$_2$ recovered from the separation, a remaining portion of the syngas and additional imported CO$_2$.

In the alternate embodiment shown in FIG. 5, the CO available for acetic acid manufacture is increased by diverting a much larger portion of the syngas from line 18 via line 20 to the $CO_2$ removal unit 22, than in the embodiment of FIG. 2. This increases the requirement for CO needed for the methanol synthesis unit 12. However, the CO requirement for the methanol synthesis unit 12 can also be met by supplying $CO_2$, although the hydrogen required for methanol synthesis with $CO_2$ is higher. The $CO_2$ stream 24 from the $CO_2$ removal unit 22 is thus supplied to methanol synthesis unit 12 instead of reformer 10 as in the FIG. 2 embodiment. Additional CO or $CO_2$, or a mixture of $CO/CO_2$, as needed for the methanol synthesis 12 can be supplied from another source (not shown) via line 25. It is preferred to import $CO_2$ instead of CO because $CO_2$ is usually easier to produce and transport than CO, and it is also less toxic. Some of the hydrogen obtained in line 32 from the CO separation unit 28 can be supplied via line 35 to the methanol synthesis unit 12. Since the amount of hydrogen in line 32 is generally greater than the amount of hydrogen required for methanol synthesis unit 12, even when using $CO_2$ as a feedstock in place of CO, the excess hydrogen via line 37 can be exported for another use, such as, for example, ammonia synthesis or combustion as a fuel gas.

Figure 6:
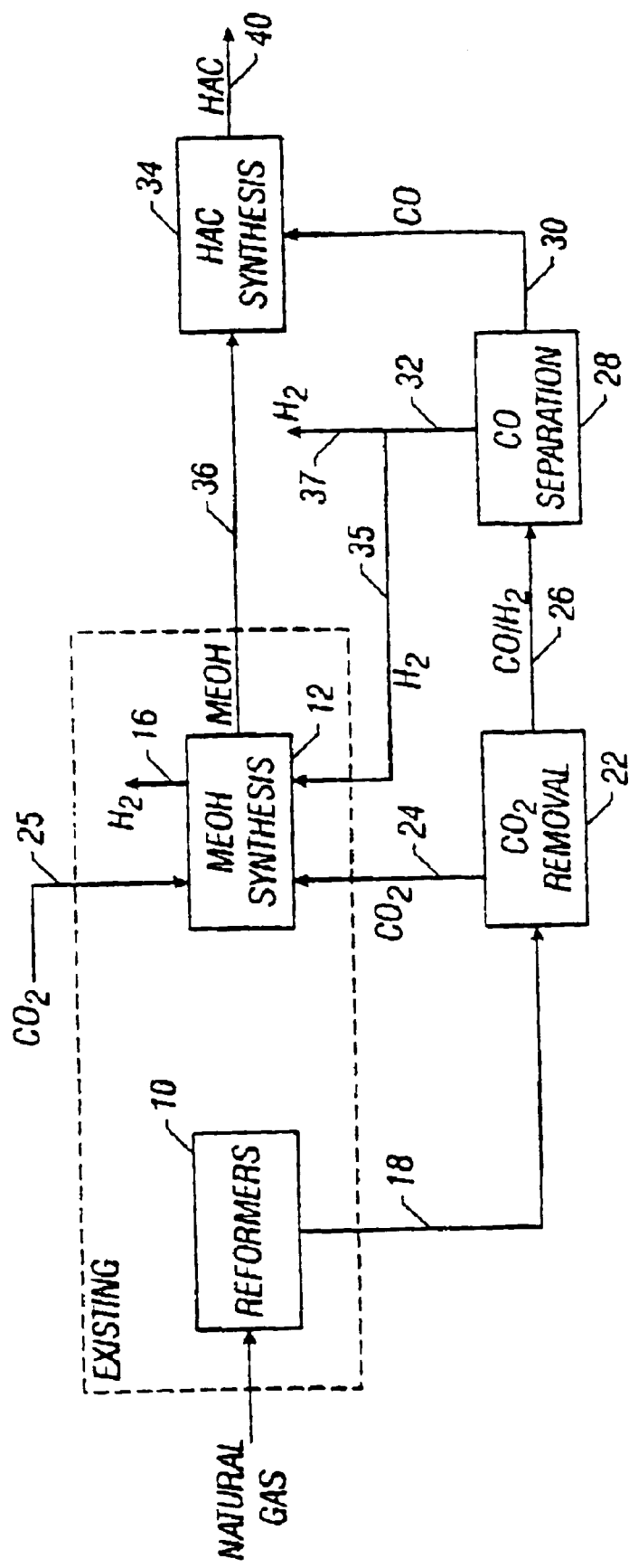
FIG. 6 is an overall block flow diagram of the plant of FIG. 1 after it has been retrofitted according to another alternate embodiment of the present invention wherein all of the syngas stream is diverted to separation and the MeOH synthesis loop is supplied with hydrogen and CO$_2$ recovered from the separation and additional imported CO$_2$.

The embodiment of FIG. 5 can have advantages over that of FIG. 2 in that the retrofit does not require modification of the reformers 10, and the methanol synthesis unit 12 can be operated at essentially design capacity without significantly changing any stream compositions in the methanol synthesis unit 12. Furthermore, the embodiment of FIG. 5 can be operated without excess methanol production, while at the same time producing hydrogen via line 37 for export The embodiment of FIG. 6 is similar to FIG. 5 except that there is no syngas supplied to the methanol synthesis unit 12, and it is instead supplied in its entirety to the $CO_2$ removal unit 22. This has the further advantage of maximizing CO and acetic acid production with slightly higher $CO_2$ import requirements and slightly less hydrogen production via line 37.

EXAMPLE 1

The retrofit of an existing methanol plant includes its reconfiguration to produce methanol and CO in stoichiometric ratio for acetic acid manufacture while still producing hydrogen at least sufficient for existing ammonia synthesis. The original plant converts 760 MTPD of natural gas in a single-pass reformer with a steam:carbon molar ratio of 2.8 to form 1760 MTPD synthesis gas containing 74.1 mol % hydrogen, 15.5 mol % CO, 7.1 mol % $CO_2$, 3.1 mol % methane, 0.2 mol % nitrogen, dry basis, which is added to the methanol synthesis loop. The feed to the methanol synthesis reactor in the original plant (recycle plus makeup synthesis gas) is 5600 MTPD of a feed gas comprising 82.2 mol % hydrogen, 9 mol % methane, 4.8 mol % CO, 3 mol % $CO_2$, 0.6 mol % nitrogen, and 0.4 mol % MeOH and other constituents, dry basis. The synthesis gas is converted in the original plant to 1560 MTPD crude methanol which is refined by distillation to give 1335 MTPD of refined product. The net loop purge gas (raw hydrogen gas for ammonia synthesis) in the original plant comprises 84.3 mol % hydrogen, 10.5 mol % methane, 2.2 mol % CO, 2 mol % $CO_2$, 0.7 mol % nitrogen, 0.4 mol % MeOH and other constituents, dry basis, and is sufficient for ammonia production in the original plant of 500 MTPD.

Figure 3:
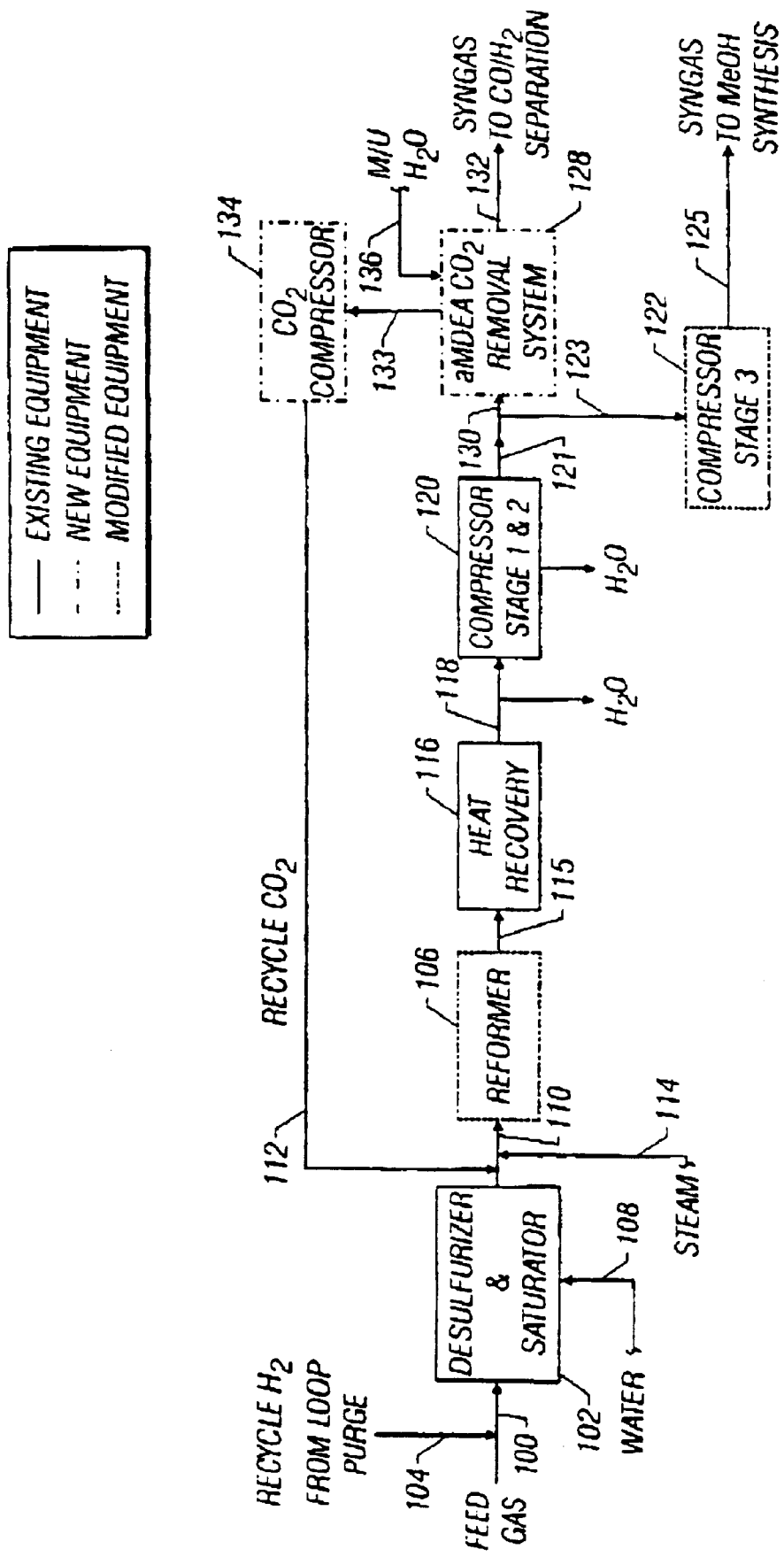
FIG. 3 is a simplified schematic process flow diagram of the front end of the plant of FIG. 2 showing the synthesis gas production and $CO_2$ recycle in the retrofitted plant wherein existing equipment is shown as a solid line, new equipment as a dash-dot-dash line, and modified equipment as a dotted line.
Figure 4:
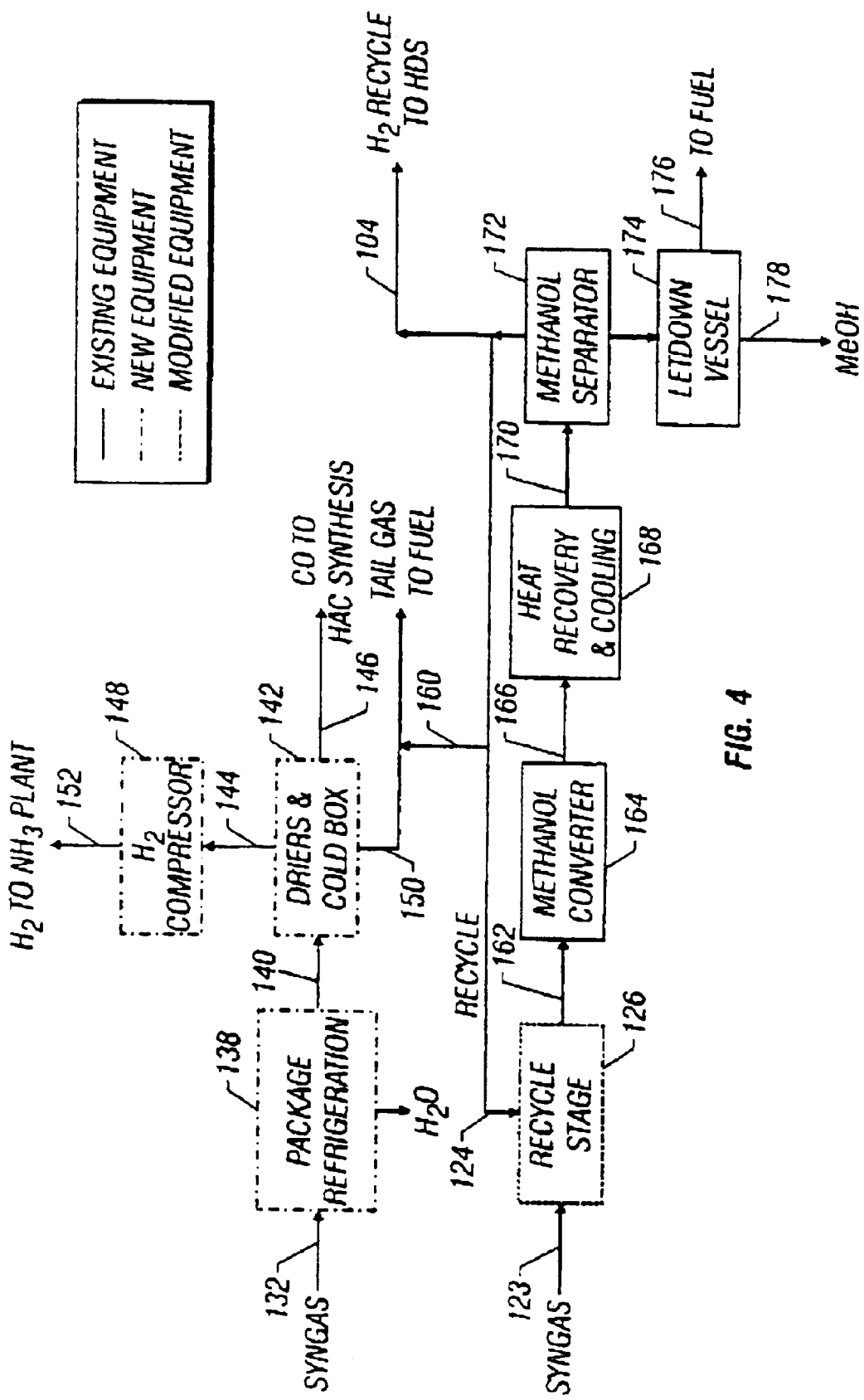
FIG. 4 is a simplified schematic process flow diagram of a portion of the plant of FIG. 2 showing the CO/H$_2$ separation and the methanol synthesis in the retrofitted plant wherein existing equipment is shown as a solid line, new equipment as a dash-dot-dash line, and modified equipment as a dotted line.

The original plant is retrofitted in accordance with FIGS. 3 and 4 to produce 760 MTPD methanol and 606 MTPD CO which can make 1208 MTPD acetic acid, and 331 MTPD hydrogen which can make 1085 MTPD ammonia. The existing reformer 106 is modified to add a new induced draft fan (not shown) and larger steam superheat, mixed feed and feed coils (not shown). The existing third stage synthesis gas compressor 122 is modified for a lower throughput by replacing the inner bundle including rotor and diaphragms. The existing synthesis gas recirculation compressor 126 is similarly modified for a low r flow rate by replacing the inner bundle including rotor and diaphragms. A new aMDEA $CO_2$ removal unit 128, a new package refrigeration unit 138, a new cold box unit 142 including driers and CO compressor, a new $CO_2$ compressor 134 to recycle $CO_2$ to the reformer 106 and new hydrogen compressors 148 to supply hydrogen to the existing ammonia plant (not shown) and a new 600 MTPD ammonia plant (not shown) are added. Prior to and/or during the retrofit (at least while the existing equipment is operational, before shutdown construction), the methanol plant can be operated at a reduced rate, bypassing approximately 27% of the synthesis gas from the discharge of the synthesis gas compressor 122 directly to the existing ammonia plant.

Advantages of the retrofit compared to a completely new CO/MeOH plant are the use of existing units and equipment, such as desulfurization, reforming including waste heat recovery, synthesis gas compressor and circulator, etc. Additional advantage is provided by the use of the existing offsite and infrastructure such as steam generation, water treatment, cooling water system, control room and product loading facilities.

With reference to FIG. 3 which shows a block flow diagram for the retrofitted plant, natural gas is supplied in line 100 to desulfurizer/saturator unit 102. The existing sulfur removal system is used to remove any $H_2S$ and organic sulfur from the process feed gas. This gas is mixed with a recycle stream 104 of hydrogen-rich synthesis gas to provide a hydrogen content of 2.4 mol %, and is heated in the desulfurizer heat exchanger (not shown) and in the convection section 116 of the reformer 106 to a temperature of 330° C. The heated gas enters the desulfurizer unit 102 where organic sulfur compounds are .first hydrogenated to hydrogen sulfide over a bed of nickel/molybdenum catalyst (not shown). Below the NiMo catalyst is a bed of zinc oxide adsorbent (not shown) in which the hydrogen sulfide is reacted to form zinc sulfide.

The desulfurized feed is passed through the existing saturator where the gas, is saturated with water from line 108 to reduce the process steam requirement. The gas exiting the saturator in line 110 is mixed with recycle carbon dioxide in line 112 and medium-pressure steam from line 114 so that the mixed gas has 3 moles of equivalent steam per mole of carbon, where equivalent steam is calculated as moles of steam plus 0.6 times moles of carbon dioxide.

Addition of $CO_2$ to the feed gas is a modification of the existing operation of the reformer 106. This produces more CO and balances the synthesis gas composition in effluent stream 115 for more efficient methanol production as described above. The mixed feed is preheated in the modified mixed feed coils (not shown) in the reformer 106 to 515° C.

The hot mixed feed is distributed to the reformer 106 catalyst tubes (not shown), passes down through the nickel reforming catalyst, and reacts to form hydrogen, CO and $CO_2$. Pressure and temperature at the outlet of the catalyst tubes is 19 bars (absolute) and 880° C. The heat recovery unit 116 is a convection section of the reformer 106 and includes coils for the high pressure steam boiler, high pressure steam superheating (modified in the retrofitted plant), mixed feed preheating (modified in the retrofitted plant), feed gas preheating (modified in the retrofitted plant), and combustion air preheating. As mentioned above, modified coils are provided for steam superheating, mixed feed preheating and feed gas preheating services. The reformer 106 includes a new induced draft fan. The old induced draft fan is used as the forced draft fan in the retrofitted plant. The reformer effluent 115 is used to generate steam, preheat boiler feed water, and provide heat in the reboilers for the topping and refining columns in the existing exchangers (not shown).

The synthesis gas in line 118 is compressed from 17.3 bars (absolute) to 41.7 bars (absolute) in the first casing of the existing synthesis compressor (first and second stages 120) without modification. The gas in discharge line 121 is then split so that 62% goes to the $CO/H_2$ production via line 130 and the rest is sent via line 123 to the second casing (third stage compressor 122 supplying syngas to line 125 for MeOH synthesis). The third compressor stage 122 of the synthesis gas compressor handles only 40% of the flow of the original plant This casing is modified with a new inner bundle including rotor and diaphragms. The gas is then cooled in the original third inter-stage cooler (not shown) and water is separated in the original inter-stage separator (not shown). The make-up gas in line 125 is then mixed with recycle gas from line 124 (see FIG. 4) and compressed in recycle circulator 126 to 80 bars (absolute). The circulator 126 will also handle only 61% of the original flow and therefore requires a new inner bundle including rotor and diaphragms.

Sixty-two percent of the gas from the second stage of the synthesis gas compressor 120 is sent via line 130 to a new aMDEA $CO_2$ removal system 128. This is a single-stage aMDEA system licensed from BASF in which the circulating solution is 40 wt % aMDEA, designed to reduce the carbon dioxide content in the gas stream 130 from 9.7 vol % to 100 ppmv, on a dry basis, in line 132. The absorber (not shown) is operated at 35° to 40° C. and 39.5 bars (absolute). The absorber overhead gas (not shown) enters a knockout drum (not shown) for separation of any entrained solution. The rich solution from the absorber bottom passes through a hydraulic turbine (not shown) for power recovery. The turbine produces power to help drive one of the lean solution pumps (not shown). The solution then enters a stripper (not shown) designed in three sections: a contact cooler on top, a low-pressure (LP) flash section in the middle, and a stripper section in the bottom. The rich solution from the hydraulic turbine enters the LP flash section which promotes $CO_2$ flashing by pressure reduction. A semi-lean solution pump (not shown) pumps the solution from the bottom of the UP flash section through the lean/semi-lean solution exchanger (not shown) to the top of the stripper section. The exchanger recovers heat from the lean solution leaving the stripper section. The solution leaving the stripper section is reboiled by low-pressure steam in a $CO_2$ stripper steam reboiler (not shown). The carbon dioxide and steam from the LP flash section is cooled to 35° C. in the contact cooler section. This is accomplished by contact with cooling water. Cooled carbon dioxide having a purity of at least 99 vol % on a dry basis is sent via line 133 to new $CO_2$ compressor 134, a four-stage, motor-driven, integrally geared turbo compressor which discharges the $CO_2$ into line 112 at 26 bars (absolute) for recycle to the reformer 106 upstream from the mixed feed coil as mentioned previously. The regenerated lean solution is cooled in the lean/semi-lean solution exchanger and then by cooling water. The cooled lean solution is pumped to the top section of the absorber, and a slipstream can be filtered to remove solids. Make-up water is added to the system via line 136.

The synthesis gas in line 132 is cooled to 4.4° C. in new package refrigeration unit 138 (see FIG. 4) which uses a screw compressor and ammonia as refrigerant. The chilled synthesis gas from the unit 138 is then passed via line 140 into driers/cold box unit 142 where it is dried and separated cryogenically into noncondensed hydrogen stream 144 and CO stream 146. The driers (not shown) are parallel beds packed with molecular sieve, one of which is on line while the other is being regenerated. In the driers, the moisture content of the gas is reduced, below 0.5 ppmv and the carbon dioxide content is reduced below 1 ppmv. Each drier can normally operate 12 hours and regeneration with hot (288° C.) reject gas from the $CO/H_2$ plant and cooling takes 6 hours, allowing 6 hours of stand-by.

The separation of CO and $H_2$ in the cold box employs a partial condensation process using two columns (not shown). The dried gas from the driers is cooled and partially liquefied in feed/effluent exchangers (not shown). The liquid is separated out, while the hydrogen product is superheated and expanded in a hydrogen expansion turbine (not shown). Cold gas from the turbine at 19.5 bars (absolute) is re-heated in the feed/effluent exchangers and leaves the cryogenic unit at 19.0 bars (absolute) and 10° C. via line 144. The liquid that was separated out, rich in CO, is flashed into a hydrogen reject column (not shown). Flash gas containing mostly hydrogen is taken from the top of the column, and re-heated in the feed/effluent exchangers to the same temperature and pressure as the gas from the turbine with which it is mixed in line 14 for supply to the hydrogen compressor 148.

Reboil for the hydrogen reject column is provided by condensing high pressure CO in a reboiler (not shown). The bottom product from the hydrogen reject column, now lean in hydrogen but containing excess methane, is flashed into a $CO/CH_4$ column (not shown) where $CH_4$ is separated from the CO and exits the column as a liquid bottoms product. The liquid methane is evaporated and heated to ambient in the feed/effluent exchangers and exits the unit 142 at 3.15 bars (absolute) as fuel gas via line 150. The CO from the top of the $CO/CH_4$ column is heated in the feed/effluent exchangers and compressed in . CO compressor (not shown) into line 146. The CO compressor is also utilized in the heat pump cycle by cooling CO in one of the feed/effluent exchangers, condensing in the reboilers for the hydrogen reject and $CO/CH_4$ columns and subcooling in another one of the feed/effluent exchangers. Subcooled liquid CO is used as reflux in the $CO/CH_4$ column and as refrigerant in the feed/effluent exchangers. The evaporated CO is reheated in one of the feed/effluent exchangers before recompression in the CO compressor.

The hydrogen compressor unit 148 comprises three parallel reciprocating, non-lubricated compressors which can each compress 50% of the hydrogen produced to 80 bars (absolute) into line 152. Normally two compressors are on line and the third is a spare. The quantity of hydrogen produced in line 152 is sufficient to produce 1084 MTPD ammonia. The existing ammonia plant (not shown) requires just enough hydrogen to make 500 MTPD ammonia, so the rest of the hydrogen product is used to make 584 MTPD ammonia in a new ammonia plant (not shown). The pressure of the hydrogen required for the new ammonia plant can be more or less than 80 bars, so the hydrogen compressor pressure can be adjusted accordingly.

The make-up syngas in line 123 (see FIG. 4) is more balanced for MeOH synthesis and has a lower R ratio of 2.1 relative to the original plant. The lower R value is due to $CO_2$ reforming and results in lower circulation in recycle line 124 and in very little purge from the MeOH loop via line 160. Gas from the discharge of the recycle stage 126 flows through line 162 to original methanol converter 164 and process flows essentially follow the original process flow scheme in line 166, heat recovery and cooling unit 168, line 170, methanol separator 172, recycle line 124, letdown vessel 174, and fuel gas stream 176, at 61–65% of original operating flows. The operation of the MeOH converter 164 was simulated by Kellogg, Brown & Root to estimate the performance of the converter 164 at the new operating conditions and lower capacity. The MeOH product stream 178 from the letdown vessel 176 is 760 MTPD.

Flow rates, compositions and properties of selected streams in the retrofitted plant are listed in Table 1 below:

TABLE 1

| Stream ID | 100 | 104 | 110 | 112 | 115 | 121 | 123 | 124 |
|---|---|---|---|---|---|---|---|---|
| Dry Mole % | | | | | | | | |
| $H_2$ | — | 61.27 | 2.40 | 0.62 | 68.79 | 68.82 | 68.82 | 61.26 |
| $N_2$ | 0.70 | 2.01 | 0.60 | — | 0.18 | 0.18 | 0.18 | 2.01 |
| $CH_4$ | 93.95 | 30.53 | 72.86 | 0.01 | 2.90 | 2.90 | 2.90 | 30.54 |
| CO | — | 2.28 | 0.10 | 0.16 | 18.40 | 18.40 | 18.40 | 2.28 |
| $CO_2$ | 0.15 | 3.49 | 20.04 | 99.20 | 9.73 | 9.70 | 9.70 | 3.49 |
| $C_2H_6$ | 3.60 | — | 2.76 | — | — | — | — | — |
| $C_3H_8$ | 1.14 | — | 0.87 | — | — | — | — | — |
| $i\text{-}C_4$ | 0.14 | — | 0.11 | — | — | — | — | — |
| $n\text{-}C_4$ | 0.24 | — | 0.18 | — | — | — | — | — |
| $n\text{-}C_5$ | 0.08 | — | 0.06 | — | — | — | — | — |
| MeOH | — | 0.42 | 0.01 | — | — | — | — | 0.42 |
| Dry Flow, KMOL/HR | 2215 | 91 | 2894 | 579 | 9569 | 9565 | 3641 | 19839 |
| Dry Flow, KG/HR | 38088 | 817 | 64192 | 25290 | 108480 | 108330 | 41235 | 178660 |
| $H_2O$ KMOL/HR | — | — | 6820 | 4.0 | 4360 | 15.1 | 5.7 | 6.8 |
| Total Flow | | | | | | | | |
| KMOL/HR | 2215 | 91 | 9713 | 582 | 13929 | 9580 | 3647 | 19846 |
| KG/HR | 38088 | 817 | 187047 | 25362 | 187047 | 108600 | 41338 | 178780 |
| Temperature, °C | 10.0 | 35.0 | 515.0 | 146.3 | 880.0 | 35.0 | 35.0 | 35.0 |
| Pressure, bar(a) | 62.0 | 25.0 | 22.3 | 26.0 | 19.0 | 41.2 | 41.2 | 79.3 |
| Density, KG/M³ | 52.54 | 7.87 | 6.58 | 33.64 | 2.65 | 17.96 | 17.96 | 27.29 |
| Average MW | 17.20 | 9.00 | 19.26 | 43.54 | 13.43 | 11.34 | 11.34 | 9.01 |

| Stream ID | 130 | 132 | 144 | 146 | 162 | 166 | 178 |
|---|---|---|---|---|---|---|---|
| Dry Mole % | | | | | | | |
| $H_2$ | 68.82 | 76.20 | 95.30 | 0.09 | 62.44 | 58.36 | 0.02 |
| $N_2$ | 0.18 | 0.20 | 0.09 | 0.83 | 1.73 | 1.91 | — |
| $CH_4$ | 2.90 | 3.21 | 0.06 | 0.08 | 26.25 | 29.11 | 0.10 |
| CO | 18.40 | 20.38 | 4.55 | 99.00 | 4.78 | 2.17 | — |
| $CO_2$ | 9.70 | 0.01 | — | — | 4.45 | 3.37 | 0.70 |
| $C_2H_6$ | — | — | — | — | — | — | — |
| $C_3H_8$ | — | — | — | — | — | — | — |
| $i\text{-}C_4$ | — | — | — | — | — | — | — |
| $n\text{-}C_4$ | — | — | — | — | — | — | — |
| $n\text{-}C_5$ | — | — | — | — | — | — | — |
| MeOH | — | — | — | — | 0.36 | 5.08 | 99.18 |
| Dry Flow, KMOL/HR | 5924 | 5345 | 4273 | 903 | 23480 | 21174 | 998 |
| Dry Flow, KG/HR | 67095 | 41802 | 13802 | 25272 | 219890 | 213940 | 32048 |
| $H_2O$ KMOL/HR | 9.4 | 11.0 | — | — | 10.2 | 340 | 333 |
| Total Flow | | | | | | | |
| KMOL/HR | 5933 | 5356 | 4273 | 903 | 23490 | 21514 | 1331 |
| KG/HR | 67262 | 42001 | 13802 | 25272 | 220070 | 220070 | 38047 |
| Temperature, °C | 35.0 | 40.0 | 10.0 | 35.0 | 41.8 | 270.0 | 35.0 |
| Pressure, bar(a) | 41.2 | 39.5 | 19.0 | 35.0 | 84.2 | 78.0 | 6.0 |
| Density, KG/M³ | 17.96 | 11.67 | | | 29.35 | 17.05 | 823.60 |
| Average MW | 11.34 | 7.84 | 3.23 | 27.98 | 9.37 | 10.23 | 28.58 |

EXAMPLE 2

An existing methanol plant is reconfigured to produce methanol and CO in a stoichiometric ratio for the manufacture of 1,000,000 metric tons/year of acetic acid in accordance with the embodiment of FIG. 5. Assuming 340 days/year of s production, this is 2040 kmol/h of acetic acid, which requires 2040 kmol/h MeOH and 2040 kmol/h CO.

Assume the original plant converts natural gas in two single-pass reformers 10 to form synthesis gas containing 11,660 kmol/h hydrogen, 2180 kmol/hr CO, and 1290 kmol/h $CO_2$. To produce the desired quantity of acetic acid, enough syngas to obtain 2040 kmol/h of CO from the new CO separation unit 28 has to be diverted from the feed to the existing methanol synthesis unit 12 to the new $CO_2$ removal unit 22. This leaves 140 kmol/h CO in the remaining syngas for feed to the methanol synthesis unit 12. To make 2040 kmol/h MeOH, there is needed a total of 2040 kmol/h of any combination of CO and/or, $CO_2$. With the 140 kmol/h CO from the remaining syngas in line 38, and 1290 kmol/h $CO_2$ from the remaining syngas in line 38, as well as the $CO_2$ from the $CO_2$ removal unit 22 via line 24, an additional 610 kmol/h $CO_2$ is needed. This $CO_2$ is imported via new line 25.

To produce the methanol in methanol synthesis unit 12, there are needed two moles of hydrogen for each mole of CO feed, as well as three moles of hydrogen for each mole of $CO_2$ feed, or (2)(140)+(3)(1290+610)=5980 kmol/h $H_2$. The two existing reformers 10 produce 11,660 kmol/h, leaving 5680 kmol/h hydrogen for export.

EXAMPLE 3

The existing methanol plant of Example 2 is reconfigured to produce methanol and CO in a stoichiometric ratio for the manufacture of the maximum quantity of acetic acid in accordance with the embodiment of FIG. 6, i.e. by supplying all of the syngas from the reformers 10 to the new $CO_2$ removal unit 22. By converting all of the available CO (2180 kmol/hr) to acetic acid, the acetic acid production is 2180 kmol/h or $1.07 \times 10^6$ metric tons/year.

To make 2180 kmol/h MeOH, there is needed a total of 2180 kmol/h of any combination of CO and/or $CO_2$. With no CO from the syngas, and 1290 kmol/h $CO_2$ from the $CO_2$ removal unit 22 via line 24, an additional 890 kmol/h $CO_2$ is needed. This $CO_2$ is imported via line 25.

To produce the methanol in methanol synthesis unit 12, there are needed three moles of hydrogen for each mole of $CO_2$ feed, or $(3)(2180)=6540$ kmol/h $H_2$. The two reformers produce 11,660 kmol/h, leaving 5120 kmol/h hydrogen for export.

What is claimed is:

1. A process for making a product, comprising the steps of:
   reforming a hydrocarbon with steam to form a syngas containing hydrogen, carbon monoxide, and carbon dioxide;
   processing the syngas in a separation unit to separate a carbon monoxide-rich stream, a hydrogen-rich stream, and a carbon dioxide-rich stream;
   operating a methanol synthesis loop to react a first portion of the hydrogen-rich stream from the separation unit with a feed stream comprising a major portion of carbon dioxide and an optional minor portion of carbon monoxide to obtain a methanol stream, wherein the carbon dioxide is supplied from the separation unit and from another source;
   reacting the carbon monoxide-rich stream from the separation unit with the methanol stream from the methanol synthesis loop to form a product selected from the group consisting of acetic acid, acetic anhydride, methyl formate, methyl acetate and combinations thereof.

2. A process for making hydrogen and a product selected from the group consisting of acetic acid, acetic anhydride, methyl formate, methyl acetate and combinations thereof; from a hydrocarbon via methanol and carbon monoxide, comprising the step of:
   catalytically reforming the hydrocarbon with steam in the presence of a minor proportion of carbon dioxide to form a syngas containing hydrogen, carbon monoxide, and carbon dioxide, wherein the syngas has a molar R ratio $((H_2-CO_2)/(CO+CO_2))$ from 2.0 to 2.9;
   diverting a major portion or the syngas to a separation unit;
   separating the syngas diverted to the separation unit into a carbon dioxide-rich stream, a carbon monoxide-rich stream and a hydrogen-rich stream;
   recycling the carbon dioxide-rich stream to the reforming step;
   operating a methanol synthesis loop to convert the hydrogen, carbon monoxide and carbon dioxide in the remaining minor portion of the syngas into a methanol stream; and
   reacting the carbon monoxide-rich stream from the separation unit with the methanol stream from the methanol synthesis loop to form a product selected from the group consisting of acetic acid, acetic anhydride, methyl formate, methyl acetate and combinations thereof, wherein the diversion step is balanced to obtain approximately stoichiometric amounts of carbon monoxide and methanol.

3. The process of claim 2 wherein the methanol synthesis loop is operated below a total maximum capacity of all methanol synthesis reactors in said loop.

4. The process of claim 2 further comprising the step of reacting the hydrogen in the hydrogen-rich stream with nitrogen in an ammonia synthesis reactor to make ammonia.

5. The process of claim 4 further comprising the step of separating air into a nitrogen stream and an oxygen stream and supplying the nitrogen stream to the ammonia synthesis reactor.

6. The process of claim 5 wherein the product comprises acetic acid or an acetic acid precursor which is converted to acetic acid, and further comprising the step of supplying the oxygen stream from the air separation unit to a vinyl acetate synthesis reactor, along with a procedure of the acetic acid from the carbon monoxide-methanol reaction step, and ethylene, to produce a vinyl acetate monomer stream.

7. The process of claim 2 wherein a molar ratio of carbon dioxide to hydrocarbon comprising natural gas in feed to the reforming step is from about 0.1 to about 0.5.

8. The process of claim 2 wherein the product comprises acetic acid and the reaction step comprises reacting methanol, methyl formate, or a combination thereof in the presence of a reaction mixture comprising carbon monoxide, water, a solvent and a catalyst system comprising at least one halogenated promoter and at least one compound of rhodium, iridium or a combination thereof.

9. The process of claim 8 wherein the reaction mixture has a water content up to 20 weight percent.

10. The process of claim 9 wherein the reaction step comprises simple carbonylation and the water content in the reaction mixture is from about 14 to about 15% weight percent.

11. The process of claim 9 wherein the reaction step comprises low-water carbonylation and the water content in the reaction mixture is from about 2 to about 8 weight percent.

12. The process of claim 9 wherein the reaction step comprises methyl formate isomerization or a combination of said isomerization and methanol carbonylation and the reaction mixture containing a nonzero quantity of water up to 2 weight percent.

13. The process of claim 9 wherein the reaction step is continuous.

14. The process of claim 2 wherein the reaction step comprises the intermediate formation of methyl formate and isomerization of the methyl formate to acetic acid.

15. The process of claim 2 wherein the reaction step comprises the intermediate reaction of CO and two moles of methyl alcohol to form methyl acetate and hydrolysis of the methyl acetate to acetic acid and methanol.

16. The process of claim 2 wherein the hydrogen-rich stream is solely an export hydrogen-rich stream.

* * * * *